US011517890B2

(12) United States Patent
Franke et al.

(10) Patent No.: US 11,517,890 B2
(45) Date of Patent: Dec. 6, 2022

(54) RU-CATALYSED DOMINO HYDROFORMYLATION / HYDROGENATION / ESTERIFICATION USING IMIDAZOLE LIGANDS

(71) Applicant: EVONIK OPERATIONS GMBH, Essen (DE)

(72) Inventors: Robert Franke, Marl (DE); Peter Kucmierczyk, Herne (DE); Matthias Beller, Ostseebad Nienhagen (DE); Ricarda Dühren, Rostock (DE); Ralf Jackstell, Rostock (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

(21) Appl. No.: 17/530,620

(22) Filed: Nov. 19, 2021

(65) Prior Publication Data

US 2022/0161244 A1 May 26, 2022

(30) Foreign Application Priority Data

Nov. 23, 2020 (EP) .................................... 20209158

(51) Int. Cl.

| | |
|---|---|
| ***B01J 31/18*** | (2006.01) |
| ***B01J 31/22*** | (2006.01) |
| ***C07C 67/035*** | (2006.01) |

(52) U.S. Cl.

CPC ....... *B01J 31/1845* (2013.01); *B01J 31/2208* (2013.01); *C07C 67/035* (2013.01); *B01J 2531/821* (2013.01)

(58) Field of Classification Search

None

See application file for complete search history.

(56) References Cited

FOREIGN PATENT DOCUMENTS

EP 0 329 252 B1 6/1992

OTHER PUBLICATIONS

U.S. Appl. No. 17/530,629, filed Nov. 19, 2021, Kucmierczyk, et al.

European Search Report dated May 12, 2021 for European Patent Application No. 20209158.3 (8 pages in German with Machine Translation).

Fleischer, I., et al. From Olefins to Alcohols: Efficient and Regioselective Ruthenium-Catalyzed Domino Hydroformylation/Reduction Sequence. Angewandte Chemie International Edition. 2013, vol. 52, pp. 2949-2953.

*Primary Examiner* — Yun Qian

(74) *Attorney, Agent, or Firm* — Smith, Gambrell & Russell, LLP

(57) ABSTRACT

Ru-catalysed domino hydroformylation/hydrogenation/esterification using imidazole ligands.

15 Claims, No Drawings

RU-CATALYSED DOMINO HYDROFORMYLATION / HYDROGENATION / ESTERIFICATION USING IMIDAZOLE LIGANDS

The present invention relates to a Ru-catalysed domino hydroformylation/hydrogenation/esterification using imidazole ligands.

EP 0 329 252 B1 describes a process for producing carboxylic acids or esters. The process is catalysed through the use of a ruthenium compound in combination with an acidic compound. The acidic compound comprises one of the following elements: phosphorus, antimony, arsenic, molybdenum, tungsten.

I. Fleischer, K. M. Dyballa, R. Jennerjahn, R. Jackstell, R. Franke, A. Spannenberg, M. Beller, “From Olefins to Alcohols: Efficient and Regioselective Ruthenium-Catalyzed Domino Hydroformylation/Reduction Sequence”, Angew. Chem. Int. Ed. 2013, 52, 2949-2953 describes a process for hydroformylation and subsequent reduction. The employed olefin is converted to the aldehyde and finally reduced to the alcohol.

The technical problem addressed by the present invention is that of providing a process which starting from an olefin results directly in an ester without isolation of intermediates. The original olefin is to form the alcohol part of the ester, i.e. the part bonded to the carbon atom of the C═O group via the oxygen. The alcohol part of the ester is moreover to have one more carbon than the employed olefin.

This problem is solved by a process according to claim 1.

Process comprising the process steps of:

a) initially charging an ethylenically unsaturated compound;

b) adding a ligand of formula (I):

(I)

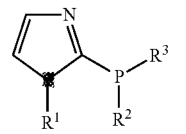

wherein $R^1$ is selected from: —($C_1$-$C_{12}$)-alkyl, —($C_6$-$C_{12}$)-cycloalkyl, —($C_6$-$C_{20}$)-aryl, —($C_5$-$C_{20}$)-heterearyl, wherein the —($C_6$-$C_{12}$)-cycloalkyl radical, the —($C_6$-$C_{20}$)-aryl radical and the —($C_6$-$C_{20}$)-heteroaryl radical may have substituents which are selected from: —($C_1$-$C_{12}$)-alkyl, —O—($C_1$-$0_1$9)-alkyl;

$R^2$ and $R^3$ are selected from: —($C_1$-$C_{12}$)-alkyl, —($C_6$-$C_{12}$)-cycloalkyl, -($C_6$-$C_{20}$)-aryl; wherein the —($C_6$-$C_{12}$)-cycloalkyl radical and the —($C_6$-$C_{20}$)-aryl radical may have substituents which are selected from: —($C_1$-$C_{12}$)-alkyl, —O—($C_1$-$C_{12}$)-alkyl; and a compound comprising Ru;

c) adding an acid (II) having the formula (IIa) or (IIb):

(IIa)

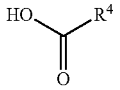

wherein $R^4$ is —($C_1$-$C_{18}$)-alkyl;

(IIb)

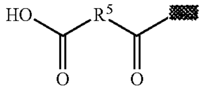

wherein $R^5$ is —($C_1$-$C_{18}$)-alkyl;

d1) feeding in CO;

e) heating the reaction mixture from a) to d) to convert the ethylenically unsaturated compound directly into an ester or diester of acid (II) without isolation of intermediates.

Step d) comprises process step d1) and optionally further process steps d2), d3) and d4), In this process, process steps a), b), c) and d) can be effected in any desired sequence. Typically, however, the addition of CO is effected after the co-reactants have been initially charged in steps a) to c). Steps d) and e) can be effected simultaneously or successively, In addition, CO can also be fed in in two or more steps, in such a way that, for example, a portion of the CO is first fed in, then the mixture is heated, and then a further portion of CO is fed in.

The expression ($C_1$-$C_{12}$)-alkyl encompasses straight-chain and branched alkyl croups having 1 to 12 carbon atoms. Suitable ($C_1$-$C_{12}$)-alkyl groups are especially methyl, ethyl, propyl, isopropyl, n-butyl, isobutyl, sec--butyl, tent-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methyipentyl, 1 ,1-dimethylbutyl, 1 ,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression ($C_6$-$C_{12}$)-cycloalkyl encompasses mono-, bi- or tricyclic hydrocarbyl groups.

The expression ($C_6$-$C_{20}$)-aryl encompasses mono- or polycyclic aromatic hydrocarbyl radicals having 6 to 20 carbon atoms. These are preferably ($C_6$-$C_{14}$)-aryl, more preferably ($C_6$-$C_{20}$)-aryl.

Suitable ($C_6$-$C_{20}$)-aryl groups are especially phenyl, naphthyl, indenyl, fluorenyl, anthracenyl, phenanthrenyl, naphthacenyl, chrysenyl, pyrenyl, coronenyl. Preferred ($C_6$-$C_{20}$)-aryl groups are phenyl, naphthyl and anthracenyl.

The expression ($C_6$-$C_{20}$)-heteroaryi encompasses mono- or polycyclic aromatic hydrocarbon radicals having 5 to 20 carbon atoms, wherein one or more of the carbon atoms are replaced by heteroatoms. Preferred heteroatoms are N, O and S. The ($C_5$-$C_{20}$)-heteroaryl groups have 5 to 20, preferably 5 or 6, ring atoms, Thus, for example, pyridyl is in the context of this invention a $C_6$-heteroaryl radical and furyl is a $C_5$-heteroaryl radical.

Suitable ($C_5$-$C_{20}$)-heteroaryi groups are especially furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

The ethylenically unsaturated compounds used as reactant in the process according to the invention contain one or more carbon-carbon double bonds. These compounds are also referred to hereinafter as olefins for simplification. The double bonds may be terminal or internal. The ethylenically unsaturated compounds preferably have a carbon-carbon double bond.

Preference is given to ethylenically unsaturated compounds having 2 to 30 carbon atoms, preferably 2 to 22 carbon atoms, more preferably 2 to 12 carbon atoms.

In one embodiment, the ethylenically unsaturated compound is selected from: ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetrarnethylethylene, heptene, 1-octene, 2-octene, di-n-butene, or mixtures thereof. In one embodiment, $R^1$ is selected from: —($C_1$-$C_{12}$)-alkyl, —($C_6$-$C_{20}$)-aryl, -($C_5$-$C_{20}$)-heteroaryl.

In one embodiment, $R^2$ and $R^3$ are —($C_3$-$C_{12}$)-cycloalkyl.

In one embodiment, $R^2$ and $R^3$ are Cy.

In one embodiment, the compound comprising Ru is selected from: $Ru_3(CO)_{12}$, $RuCl_3*H_2O$, $Ru(Cl)_2(DMSO)_4$, $Ru(acac)_3$.

In one embodiment, the compound comprising Ru is $Ru_3(CO)_{12}$.

In one embodiment, $R^4$ is —($C_1$-$C_{12}$)-alkyl.

In one embodiment, $R^4$ is —($C_1$-$C_8$)-alkyl,

In one embodiment, $R^5$ is —($C_1$-$C_{12}$)-alkyl,

In one embodiment, $R^5$ is —($C_1$-$C_8$)-alkyl,

In one embodiment, the process comprises the additional process step d2): d2) feeding in $H_2$.

In one embodiment the $H_2$ pressure is in the range from 1 MPa (10 bar) to 6 MPa (60 bar).

In one embodiment, the process comprises the additional process step d3): d3) adding $H_2O$.

in one embodiment, $H_2O$ is added in an amount such that the molar ratio of $H_2O$ to the ethylenically unsaturated compound is in the range from 1:1 to 10:1.

In one embodiment, the process comprises the additional process step d4): d4) adding para-toluenesulfonic acid.

In one embodiment, the acid (II) is added in process step c) in an amount such that the molar ratio of acid to the ethylenically unsaturated compound is in the range from 2:1 to 10:1.

In one embodiment, the acid (II) has the formula (IIa).

In one embodiment, the acid (II) has the formula (IIb).

In one embodiment, the ligand in process step b) is selected from:

(1)

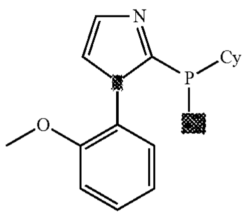

(2)

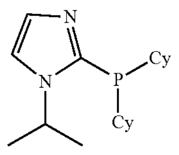

(3)

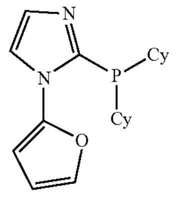

-continued (4)

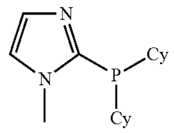

(5)

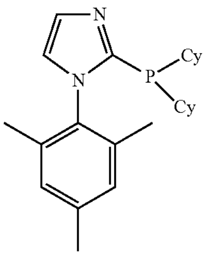

(6)

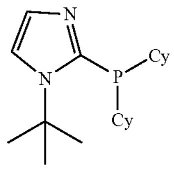

In one embodiment, the reaction mixture is in process step e) heated to a temperature between 50° C. and 180° C., preferably between 80° C. and 160° C., more preferably between 100° C. and 150° C., to convert the ethylenically unsaturated compound to the ester.

The invention is described in detail hereinafter by working examples.

General Procedures

All operations with air- and moisture-sensitive substances were performed in an argon atmosphere and with baked-out glass apparatuses using Schlenk techniques. The chemicals were obtained from commercial producers and employed as supplied, provided purity was at least 98%. Oxygen-tree and dry solvents were prepared by distillation under argon. Synthesis gas (CO:99.997%, $H_2$/CO:1:1+/−1%) was obtained from Linde.

The products were analysed by $^1$H-NMR and $^{13}$C-NMR spectroscopy. The NMR spectra were recorded on Bruker AV 400 (400 MHz), Bruker AV 300 (300 MHz) or Fourier 300 (MHz) instruments. Chemical shifts δ (ppm) are reported relative to the employed solvent: References for $CDCl_3$ were 7.26 ppm ($^1$H-NMR) and 77.16 ($^{13}$C-NMR). $^{13}$C-NMR spectra were recorded with a broadband decoupled method.

GC analyses were performed on a 7890A GC system from Agilent Technologies using a 30 m HP-5 column. The carrier gas employed was argon. The products were analysed by GC or GC-MS or isolated by column chromatography (silica, EtOAc/heptane). The GC yields were calculated by internal calibration. Hexadecane was used as an internal standard.

Performing the Catalytic Experiments

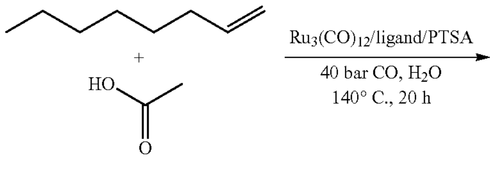

-continued

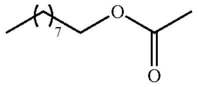

The catalytic experiments were performed in 4 mL glass vials having screwtop caps and a PTFE septum. The vials were provided with oven-dried magnetic stirrers and the connection to the gas atmosphere was made using a needle. The reaction batch comprised 2 mL. The vials were placed in a 300 mL Parr4560 autoclave and stirred using a magnetic stirrer. In the first step $Ru_3(CO)_{12}$ (5mol %), ligand (5.5 mol %) and PTSA*$H_2O$ (20.6 mol %) are weighed into the vial. The vial is sealed with a screwtop cap provided with a septum, sealed and connected to the argon atmosphere via a cannula. The vial was evacuated three times and purged with argon. Acetic acid (1.17 mL), $H_2O$ (0.35 mL) and 1-octene (3 mmol) were injected by Hamilton syringe. The vial was transferred into the autoclave under an argon atmosphere. The autoclave is tightly sealed and initially purged three times with 10 bar of CO at room temperature.

Subsequently, 40 bar of CO are applied, the autoclave is placed on a magnetic stirrer in an aluminium block and heated to 140° C. for 20 h. After 20 h, the autoclave was cooled to room temperature and the pressure was cautiously released. As internal standard 100 μL of hexadecane were introduced into the reaction solution. The yield was determined by GC analysis.

The reaction was performed under analogous conditions for the ligands (1) to (6) and for the comparative ligand (7). Since the comparative ligand (7) is a bidentate ligand only 0.55 mol % were employed instead of the 1.1 mol %.

(7)

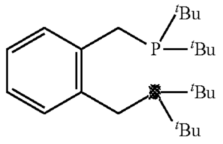

Reaction Conditions

1-Octene: 3 mmol $Ru_3(CO)_{12}$: 5 mol % Ru

Ligand (1) to (6): 5.5 mol % based on the olefin

Ligand (7): 2.75 mol % based on the olefin

PTSA*$H_2O$ using (1)-(6): 20.6 mol %

PTSA*$H_2O$ using (7): 10.3 mol %

$H_2O$: 1-octene=6.5: 1 (molar ratio)

HOAc: 1-octene=6.75: 1 (molar ratio)

CO pressure: 40 bar

Temperature: 140° C.

Reaction time: 20 h

Experimental Results

| Ligand | Ester yield [%] |
|---|---|
| (1)* | 28 |
| (2)* | 28 |
| (3)* | 24 |
| (4)* | 21 |

-continued

| Ligand | Ester yield [%] |
|---|---|
| (5)* | 25 |
| (6)* | 18 |
| (7) | 10 |

*inventive process

The invention claimed is:

1. A process comprising the process steps of:

a) initially charging an ethylenically unsaturated compound;

b) adding a ligand of formula (I):

(I)

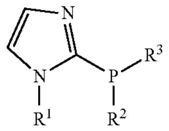

A wherein $R^1$ is selected from: —($C_1$-$C_{12}$)-alkyl, —($C_6$-$C_{12}$)-cycloalkyl, —($C_6$-$C_{20}$)-aryl or —($C_5$-$C_{20}$)-heteroaryl, wherein the —($C_6$-$C_{12}$)-cycloalkyl radical, the —($C_6$-$C_{20}$)-aryl radical and the —($C_5$-$C_{20}$)-heteroaryl radical, each may have substituents which are selected from: —($C_1$-$C_{12}$)-alkyl, —O—($C_1$-$C_{12}$)-alkyl;

$R^2$ and $R^3$ are selected from: —($C_1$-$C_{12}$)-alkyl, —($C_6$-$C_{12}$)-cycloalkyl, —($C_6$-$C_{20}$)-aryl;

wherein the —($C_6$-$C_{12}$)-cycloalkyl radical and the —($C_6$-$C_{20}$)-aryl radical, may have substituents which are selected from: —($C_1$-$C_{12}$)-alkyl, —O—($C_1$-$C_{12}$)-alkyl;

and a compound comprising Ru;

c) adding an acid (II) having the formula (IIa) or (IIb):

(IIa)

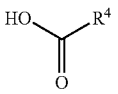

wherein $R^4$ is —($C_1$-$C_{18}$)-alkyl;

(IIb)

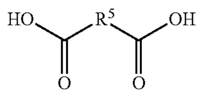

wherein $R^5$ is —($C_1$-$C_{18}$)-alkyl;

d1) feeding in CO;

e) heating the reaction mixture from a) to d) to convert the ethylenically unsaturated compound directly into an ester or diester of acid (II) without isolation of intermediates.

2. The process according to claim 1, wherein the ethylenically unsaturated compound is selected from: ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, or mixtures thereof.

3. The process according to claim 1, wherein $R^1$ is selected from: —($C_1$-$C_{12}$)-alkyl, —($C_6$-$C_{20}$)-aryl or —($C_5$-$C_{20}$) -heteroaryl.

4. The process according to claim 1, wherein $R^2$ and $R^3$ are —($C_3$-$C_{12}$)-cycloalkyl.

5. The process according to claim 1, wherein the compound comprising Ru is selected from: $Ru_3(CO)_{12}$, $RuCl_3*H_2O$, $Ru(Cl)_2(DMSO)_4$, $Ru(acac)_3$.

6. The process according to claim 1, wherein $R^4$ is —($C_1$-$C_{12}$)-alkyl.

7. The process according to claim 1, wherein $R^5$ is —($C_1$-$C_{12}$)-alkyl.

8. The process according to claim 1, comprising the additional process step d2):

d2) feeding in $H_2$.

9. The process according to claim 8, wherein the $H_2$ pressure is in the range from 1 MPa (10 bar) to 6 MPa (60 bar).

10. The process according to claim 1, comprising the additional process step d3):

d3) adding $H_2O$.

11. The process according to claim 10, wherein $H_2O$ is added in an amount such that the molar ratio of $H_2O$ to the ethylenically unsaturated compound is in the range from 1:1 to 10:1.

12. The process according to claim 1, comprising the additional process step d4):

d4) adding para-toluenesulfonic acid.

13. The process according to claim 1, wherein the acid (II) is added in process step c) in an amount such that the molar ratio of acid to the ethylenically unsaturated compound is in the range from 2:1 to 10:1.

14. The process according to claim 1, wherein the acid (II) has the formula (IIa).

15. The process according to claim 1, wherein the ligand in process step b) is selected from:

(1)

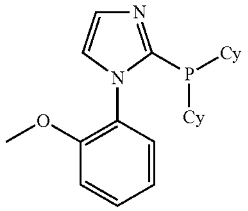

-continued (2)

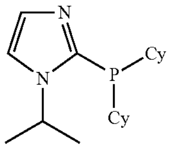

(3)

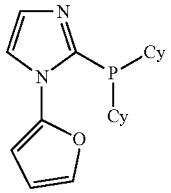

(4)

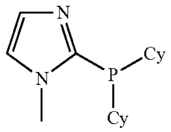

(5)

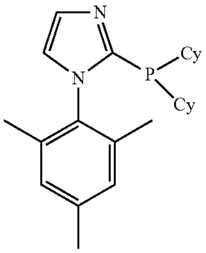

or (6)

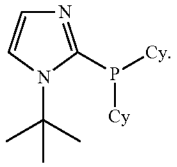

* * * * *

UNITED STATES PATENT AND TRADEMARK OFFICE

CERTIFICATE OF CORRECTION

PATENT NO. : 11,517,890 B2
APPLICATION NO. : 17/530620
DATED : December 6, 2022
INVENTOR(S) : Robert Franke et al.

It is certified that error appears in the above-identified patent and that said Letters Patent is hereby corrected as shown below:

On the Title Page

Item (72) Please add inventor Carolin SCHNEIDER (Monheim am Rhein, DE).

Signed and Sealed this
Fourteenth Day of October, 2025

John A. Squires
*Director of the United States Patent and Trademark Office*